US008962817B2

(12) United States Patent
Stewart et al.

(10) Patent No.: US 8,962,817 B2
(45) Date of Patent: Feb. 24, 2015

(54) VECTORS ENCODING A PARALYTIC PEPTIDE

(71) Applicant: Soricimed Biopharma Inc., Sackville (CA)

(72) Inventors: John M Stewart, Sackville (CA); Bradley J Steeves, Moncton (CA); Karl Vernes, Armidale (AU)

(73) Assignee: Soricimed Biopharma Inc., Sackville (CA)

( * ) Notice: Subject to any disclaimer, the term of this patent is extended or adjusted under 35 U.S.C. 154(b) by 0 days.

(21) Appl. No.: 14/207,907

(22) Filed: Mar. 13, 2014

(65) Prior Publication Data

US 2014/0273204 A1    Sep. 18, 2014

Related U.S. Application Data

(63) Continuation of application No. 13/723,320, filed on Dec. 21, 2012, now Pat. No. 8,673,858, which is a continuation of application No. 13/195,254, filed on Aug. 1, 2011, now Pat. No. 8,338,136, which is a continuation of application No. 12/792,903, filed on Jun. 3, 2010, now Pat. No. 8,003,754, which is a continuation of application No. 11/834,916, filed on Aug. 7, 2007, now Pat. No. 7,745,588, which is a continuation of application No. 11/507,128, filed on Aug. 21, 2006, now Pat. No. 7,273,850, which is a continuation of application No. 10/858,233, filed on Jun. 1, 2004, now Pat. No. 7,119,168, which is a continuation-in-part of application No. 10/716,314, filed on Nov. 18, 2003, now Pat. No. 7,485,622.

(60) Provisional application No. 60/427,682, filed on Nov. 18, 2002.

(51) Int. Cl.
*C07H 21/02* (2006.01)
*C07K 7/06* (2006.01)
*A61K 38/17* (2006.01)
*C07K 14/47* (2006.01)

(52) U.S. Cl.
CPC .............. *C07K 7/06* (2013.01); *A61K 38/1709* (2013.01); *C07K 14/47* (2013.01); *C07K 14/4703* (2013.01)
USPC ...................................... 536/23.1

(58) Field of Classification Search
None
See application file for complete search history.

(56) References Cited

U.S. PATENT DOCUMENTS

| | | |
|---|---|---|
| 5,424,286 A | 6/1995 | Eng |
| 6,326,020 B1 | 12/2001 | Kohane et al. |
| 7,119,168 B2 | 10/2006 | Stewart et al. |
| 7,273,850 B2 | 9/2007 | Stewart et al. |
| 7,485,622 B2 | 2/2009 | Stewart et al. |
| 7,745,588 B2 | 6/2010 | Stewart et al. |
| 8,003,754 B2 | 8/2011 | Stewart et al. |
| 8,338,136 B2 | 12/2012 | Stewart et al. |
| 2006/0217302 A1 | 9/2006 | Stewart et al. |

FOREIGN PATENT DOCUMENTS

JP    10236963    8/1998

OTHER PUBLICATIONS

Tedford et al, Functional significance of the beta hairpin in the insecticidal neurotoxin omega-atracotoxin-Hv1a. J Biol Chem. Jul. 13, 2001;276(28):26568-76. Epub Apr. 19, 2001.*
Amersham, Protein Purification Handbook, 1999.
Cai, Z, et al., "Solution Structure of BmBKTx1, a new BKca1 Channel Blocker from the Chinese Scorpion *Buthus martensi* Karsch," Biochemistry, vol. 433, No. 13, pp. 3764-3771, 2004.
Christenbury, P., " A Study of the Ecology of *Biarina brevicaudia* in North Carolina ando f the Effect of Shrew Toxin on the Liver and Kidneys of Mice." A thesis submitted to the Graduate Faculty of Wake Forest College in parcial fulfillment of the requirements for the negree of Master of Arts in the Department of Biology, Aug. 1966.
Dekker, E. et al., "The epithelial calcium channels, TRPV5 and TRPV6: from identification towards regulation," Cell Calcium, vol. 33, pp. 497-507, 2003.
Dufton, M., "Venomous Mammals," Pharmac. Ther. vol. 53, pp. 199-215, 1992.
Ellis, S. et al., "Properties of a Toxin from the Salivary Gland of the Shrew, *Blarina brevicuada*," The Journal of Pharmacology & Experimental Therapeutics, vol. 114, No. 2, pp. 127-137, 1955.
GenCore version 5.1.7, pp. 3-4 (Result 5), Feb. 1, 1996 (created, last sequence update), Oct. 25, 2004 (last annotation update).
George, S. et al., "*Blarina brevicuada*," Mammalian Species, No. 261, pp. 1-9, 3 Figures, 1986.
Kita, M. et al., "Blarina toxin, a mammalian lethal venom from the short-tailed shrew *Blarina brevicuada*: isolation and characterization," Proceedings of the National Academy of Sciences of the United States of America, vol. 101, No. 20, pp. 7542-7547, 2004.
Lecchi, P. et al "The Structure of Synenkephalin (Pro-Enkephalin 1-73) Is Dictated by Three Disulfide Bridges," Biochemical and Biophysical Research Communications, vol. 232, pp. 800-805, 1997.
Martin, I., "Venom of the Short-Tailed Shrew (*Blarina brevicuada*) As An Insect Immobilizing Agent," Journal of Mammalogy, vol. 62, No. 1, p009U7p. 189-192, 1978.
Montell, C., "The venerable inveterate invertebrate TRP channels," Cell Calcium, vol. 33, pp. 409-417, 2003.

(Continued)

*Primary Examiner* — Sheridan Swope
(74) *Attorney, Agent, or Firm* — Ballard Spahr LLP

(57) ABSTRACT

The invention relates to recombinant expression vectors encoding a low molecular weight peptide isolated from the submaxiliary saliva glands of shrews of the species *Blarina* as a paralytic agent. This novel paralytic agent is useful as a neuromuscular blocker and analgesic or as an insecticide.

20 Claims, 16 Drawing Sheets

(56) References Cited

OTHER PUBLICATIONS

Mount Allison University, "Potent Peptide Paralytic Agent," Version 1, Jun. 2003.

Mount Allison University, "Potent Peptide Paralytic Agent," Version 2, Jul. 2003.

Pearson, O., "On the cause and nature of poisonous action produced by the bite of a shrew (*Blarina brevicuada*)," Journal of Mammalogy, pp. 159-166, 1942.

Peng, J. et al., "CaT1 Expression Correlates with Tumor Grade in Prostate Cancer," Biochemical and Biphysical Research Communications, vol. 282, pp. 729-734, 2001.

Peng, J. et al. "Human Calcium Transport Protein CaT1," Biochemical and Biophysical Research Communications, vol. 278, pp. 326-332, 2000.

Pohl, M. et al., "Molecular Cloning of the Helodermin and Exendin-4 cDNAs in the Lizard," The Journal of Biological Chemistry, vol. 273, No. 16, pp. 9778-9784, 1998.

Pucek, M., Chemistry and Pharmacology of Insertivore Venoms, Chapter 3 of Venomous Animals and Their Venoms, edited by W. Bucheri, Academic Press, New York—London, pp. 43-50, 1968.

Smart P., "Shrew Saliva Spells Relief? Prof. Jack Stewart makes breakthrough medical discovery," The Argosy, Jan. 16, 2003.

Steeves, "Active Components of the Venumous Saliva of the Short-tailed Shrew (*Blarina brevicauda*)," Bachelor of Science Thesis, Department of Biology, Mount Allison University, May 2002 (presented Apr. 26, 2002).

"The venom of the shrew maybe in the new Botox," National Post, Science Section, Biochemisty, Dec. 20, 2002.

Tomasi, T., "Function of Venom in the Short-Tailed Shrew *Blarina brevicuada*," Journal of Mammalogy, vol. 59, No. 4, pp. 852-854, 1978.

Zhuang, L. et al., "Calcium-Selective Ion Channel, CaT1, is Apically Localized in the Gastrointestinal Tract Epithelia and is Aberrantly Expressed in Human Malignancies,"Laboratory Investigation, vol. 82, No. 12, pp. 1755-1764, 2002.

Galye et al., "Identification of regions in interleukin-1 alpha important for activity," J. Biol Chem. Oct. 15, 1993; 268 (29):22105-11.

Whisstock et al., "Prediction of Protein Function from Protein Sequence and Structure," Q Rev. Biophys. Aug. 2003; 36(3):307-40. Review.

(Author Unknown), "The Venom of the Shrew Maybe in the New Botox," National Post, Science Section, Biochemistry, Dec. 20, 2002.

* cited by examiner

DCSQDCAACS ILARPAELNT ETCILECEGK LSSNDTEGGL CKEFLHPSKV DLPR

Figure 1A

DCSQDCAACS ILARPAELNT ETCILECAGK LSSNDTEGGL CKEFLHPSKV DLPR

Figure 1B

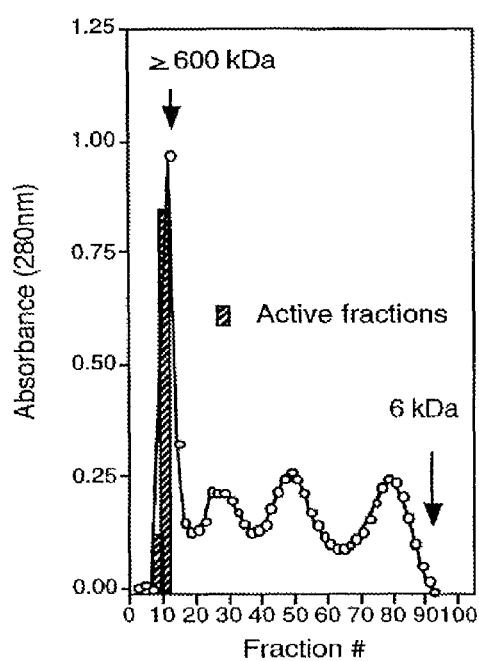
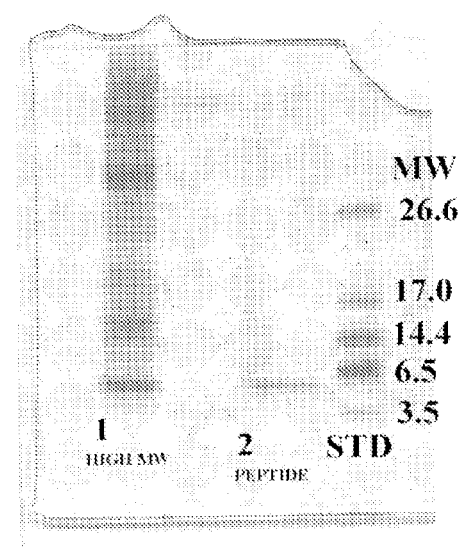
Figure 2
Figure 3

Potassium Phosphate Buffer

A			B

VECTORS ENCODING A PARALYTIC PEPTIDE

CROSS REFERENCE TO RELATED APPLICATION

This application is a continuation of U.S. application Ser. No. 13/723,320 filed Dec. 21, 2012, which is a continuation of Ser. No. 13/195,254 filed on Aug. 1, 2011 (now U.S. Pat. No. 8,338,136), which is a continuation of U.S. application Ser. No. 12/792,903 filed Jun. 3, 2010 (now U.S. Pat. No. 8,003,754), which is a continuation of U.S. application Ser. No. 11/834,916 filed on Aug. 7, 2007 (now U.S. Pat. No. 7,745,588), which is a continuation of U.S. application Ser. No. 11/507,128 filed on Aug. 21, 2006 (now U.S. Pat. No. 7,273,850), which is a continuation of U.S. application Ser. No. 10/858,233 filed on Jun. 1, 2004 (now U.S. Pat. No. 7,119,168), which is a continuation-in-part of U.S. application Ser. No. 10/716,314 filed on Nov. 18, 2003 (now U.S. Pat. No. 7,485,622), which claims priority from U.S. application No. 60/427,682, filed Nov. 18, 2002 (now expired), all of which are incorporated by reference herein in their entirety.

FIELD OF THE INVENTION

The invention relates to a paralytic peptide for neuromuscular therapy and other uses requiring disruption of neuromuscular mechanisms.

BACKGROUND OF THE INVENTION

Shrews are a very ancient group of primitive mammals that resemble most closely the proto-mammals. They are not closely related to rodents because rodents evolved from different groups of mammals. According to Dufton (1992), the known venomous species of shrew are: the northern short-tailed shrew (*Blarina brevicauda*), the Haitian solenodon (*Solenodon paradoxus*), the European water shrew (*Neomys fodiens*) and the Mediterranean shrew (*Neomys anomalous*). Another venomous shrew is the southern short-tailed shrew (*Blarina carolinensis*). It has also been suggested that the Cuban solenodon (*Apotogale cubanus*), the American shrew (*Sorex cinereus*) and the Maritime shrew (*Sorex maritimensis*) could be venomous. The northern short-tailed shrew (*Blarina brevicauda*) and its closely related species use a paralytic venom in its saliva to paralyze insects, other invertebrates (worms, annelids etc.), nesting birds and small mammals which it then stores, alive in its den, for future feeding (Martin 1981; George et al. 1986; Dufton 1992).

The shrew venom literature generally consists of seven articles from the 40s and 50s and one MA thesis in 1966 [Christenbury 1966]. These are summarized in a review [Dufton 1992]. Using a crude ammonium sulfate precipitate of shrew saliva glands, Ellis and Krayer (1955) concluded the active agent was probably a protein and, because of its inability to dialyze, a larger protein. A major contribution of the Ellis & Krayer work was to show activity in cats, dogs, mice, rats, guinea pigs and rabbits. Christenbury [1966] showed Ellis & Krayer's preparation stopped oxygen consumption by mouse kidney and liver slices. Japanese patent application (JP 10-236963; 1998) appears to disclose an alcoholic extract of saliva glands from two shrew species (*Sorex unguiculatus* & *Sorex shinto saevus*) as a calcium channel blocker and its use as a hypotensive. The purity is low—the extract includes any compounds that would dissolve in 70% ethanol. There is no information about the responsible active molecule/s in the unknown mixture of compounds.

SUMMARY OF THE INVENTION

The paralytic compound of shrew saliva remained unidentified until now. The inventors have isolated and purified a paralytic compound having the sequence shown in FIG. 1A (SEQ ID NO:1) and identified derivatives, such as the variant shown in FIG. 1B (SEQ ID NO:2) and other derivatives described herein. The inventors further show that, while a high molecular weight fraction is paralytic, the active molecule is not a large protein but, unexpectedly, a small peptide bound in a large complex of many proteins (FIG. 3, Lane 1). The invention relates to a low molecular weight peptide (or optionally a suite of related peptides), preferably, isolated and purified from the submaxiliary saliva glands (eg. submaxillary gland) or saliva of shrews of a species such as *Blarina* as a paralytic agent. The peptide optionally has a molecular weight of about 6000 Da as measured by SDDS-PAGE. The peptide optionally includes at least one or two cysteine amino acids having a sulfhydryl group and forming a disulfhydryl bond. Optionally, the peptide comprises six cysteine amino acids each having a sulfhydryl group forming three disulfhydryl bonds. The peptide optionally absorbs light at 280 nm and more strongly at 260 nm, and includes at least one aromatic amino acid. All or part of the peptide or it parent pro-peptide may also be produced by recombinant DNA methods or in vitro or in vivo peptide synthesis. This novel paralytic agent is useful as a neuromuscular blocker.

As mentioned above, the active ingredient is a small peptide isolated in an unusual and unexpected combination within a large protein complex (or a large protein). The peptide is optionally is hydrolytically cleaved from the protein or complex. Known mammalian saliva peptides (e.g. vasoactive intestinal polypeptide & glucagon-like peptide 1 [Pohl & Wank 1998]) would not be contaminants as they are discarded with inactive, low molecular weight molecules during the purification protocols. The preparation of the invention is of great purity and can be extracted from an unexpected subcellular source.

The present inventors have isolated and purified novel proteins from the submaxilary saliva glands of shrews. In accordance with one embodiment of the invention, there is provided an isolated and purified shrew saliva peptide. In a specific embodiment, the isolated and purified shrew saliva peptide has the amino acid sequence shown in FIG. 1A or derivatives thereof, such as the peptide in FIG. 1B and other derivatives described herein. The invention includes methods of isolating a paralytic compound from venomous shrew saliva gland or shrew saliva, comprising providing the gland or saliva, isolating the paralytic compound from the gland or saliva and optionally purifying the compound.

The shrew submaxillary gland or saliva is optionally isolated from *Blarina brevicauda, Blarina carolinensis, Sorex unguiculatus, Sorex shinto saevu* (*Solenodon paradoxus*), *Neomys fodiens, Sorex maritimensis* or *Neomys anomalous*. The peptide is potent, for example, i) a 10 microliter dose of 20% (w/v) crude gland extract injected into a mealworm in an in vitro assay causes mealworm paralysis in less than 1 second; and ii) a 10 microliter dose of 10% (w/v) crude gland extract injected into a mealworm in an in vitro assay causes mealworm paralysis in less than 10 seconds. The invention also includes peptides of the invention in a purified form. The peptides are optionally purified at least 90%, 95% or 99%. The invention also includes an isolated peptide comprising a fragment of 5-10, 10-15, 15-20, or 20-24 amino acids of a peptide described in this application. The invention also optionally includes pharmaceutical composition or cosmetic composition or insecticide composition including a peptide of the invention. The invention further optionally includes an isolated and purified multiprotein complex comprising the peptide of claim 1 or 2 and having a molecular weight of greater than or equal to 600,000 daltons.

Another aspect of the invention comprises a method of dissociating the peptide of the invention from a multiprotein complex described herein, comprising contacting the multiprotein complex with sodium dodecylsulfate or aqueous alcohol or warming at 40° C.

The present invention also provides a pharmaceutical composition or a cosmetic composition that includes the isolated and purified shrew saliva peptide, and the use of the peptide as a pharmaceutical substance, neuromuscular blocker or an analgesic, for example, as an analgesic for wounds. The invention is yet further directed to the use of the isolated and purified shrew saliva peptide for prevention or treatment of migraine, myofacial and other types of pain, muscle tremors, neuromuscular diseases, excessive sweating and wrinkles. The invention also optionally relates to the use of a peptide of the invention descried herein as an insect immobilizing agent or an insecticide. A peptide shown in FIG. 1A or 1B would be an example of a compound for all the aforementioned uses.

In particular, the invention is directed to a method of preventing or treating migraines, myofacial and other types of pain, muscle tremors, neuromuscular diseases, and excessive sweating in a mammal comprising administering to the mammal an isolated and purified shrew saliva peptide, for example in a pharmaceutical composition. The mammal is preferably a human. The invention is also directed to a method of providing analgesia, for example, for an analgesic for wounds, or neuromuscular blocking in a mammal comprising administering to a mammal a pharmaceutical composition including the isolated and purified shrew saliva peptide. The invention is further directed to a method of preventing or reducing wrinkles in a mammal comprising administering to the mammal the isolated and purified shrew saliva peptide, for example in a cosmetic composition. The invention is also directed to a method of killing or immobilizing an insect comprising administering to the insect a peptide of the invention, for example in an insecticidal composition, for example, by infecting insects with species-specific viruses engineered to direct the infected insect to produce the paralytic peptide (a useful virus is a Baculovirus). A peptide shown in FIG. 1A or 1B or another compound described herein would be an example of a compound suitable for all the aforementioned methods.

The invention is also directed to the use of the isolated and purified shrew saliva peptide for the preparation of antibodies, including polyclonal antibodies, monoclonal antibodies or functional fragments thereof. This invention also relates to the antibodies so produced.

The invention is yet further directed to a method of determining the potency of a paralytic agent by administering the paralytic agent to a mealworm or other insect; determining the time until onset of paralysis and/or the duration of paralysis; and wherein the time for onset of paralysis is inversely proportional to the strength of the paralytic agent and the duration of paralysis is proportional to the strength of the paralytic agent.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

These and other features of embodiments of the invention will become more apparent from the following description in which reference is made to the appended drawings wherein:

FIG. 1. Amino acid sequences: A. (SEQ ID NO:1); B. (SEQ ID NO:2).

FIG. 2. Size exclusion chromatography of shrew submaxilary gland extract with bioactive fractions indicated by crosshatching.

FIG. 3. SDS-PAGE analysis of shrew submaxilary gland extract. The small active component exists as part of a very high molecular weight complex.

DETAILED DESCRIPTION OF THE INVENTION

Figure 4:
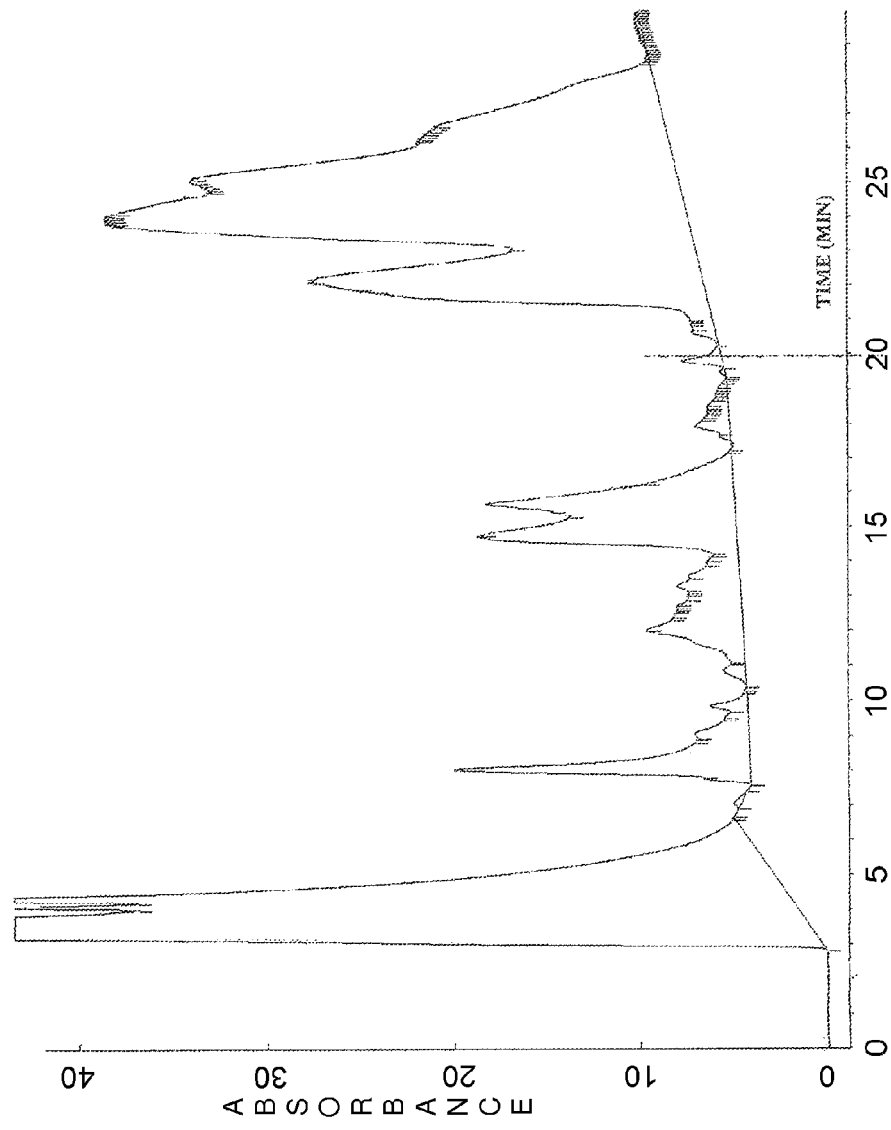
FIG. 4. First HPLC elution profile of active fraction.

The invention involves isolation and purification of a peptide paralytic agent from shrew salivary gland or saliva (called "PS peptide" or soricidin). The peptide preferably has 54 amino acids and the sequence shown in FIG. 1A (SEQ ID NO:1) or is a derivative, such as that shown in FIG. 1B (SEQ ID NO:2) or another derivative as described herein. In one embodiment, FIGS. 1A is native isolated sequence and 1B is a derivative of native sequence. Optionally the amino acid sequences are isolated and purified. The peptide may be isolated from any shrew having paralytic activity in its saliva, such as *Blarina, Neomys* and *Sorex* shrew species. The invention also optionally includes a bioassay using the common mealworm or other insect for rapid assessment of paralytic bioactivity. For example, the bioassay shows that paralytic saliva administered to the mealworm can keep it paralyzed but alive for at least 7 days. The toxin is very powerful; in dose response studies a 10 microliter injection of 20% (w/v) crude gland extracts produces total paralysis in less than 1 sec while 10% requires 10 sec for total paralysis. The 10 microliter sample represented about 8 micrograms of total soluble extracted protein (0.8 mg/mL of extract, 0.010 mL of this injected=0.008 mg=8 micrograms total soluble protein). Of this, the peptide represents (as assessed from the gel stain density) about 1/10 of the protein in the whole extract (far right lane of gel picture). Thus, the actual peptide injected represents about 0.8 micrograms of material or 800 nanograms. Using the bioassay and various chromatographic methods the inventors isolated a peptide(s) with a molecular weight of about 6000 (SDS-PAGE) that shows paralytic activity. Unexpectedly, the small active component exists as part of a very high molecular weight, multiprotein complex (FIG. 2; FIG. 3, lane 1) the molecular weight of the complex was about 600,000 daltons. It appeared in a void volume fraction from a size exclusion column (Sephadex G-200) that has a molecular weight cut-off of 600,000 daltons. After purification, the complex shows a single band on the gel (FIG. 3 lane 2). The peptide sequence is readily obtained by known techniques, such as the standard sequential Edman degradation (P. Edman and G. Begg. 1967. Eur. J. Biochem. 1: 80-91. H. D. Niall, 1973. Methods Enzymol. 27: 942-1010.) and mass spectroscopic sequence determination.

The secondary structure of soricidin, based on two dimensional structure analysis shows an alpha/beta scaffold. The disulfide linkage pattern (2-23; 6-27; 9-41) was determined by comparison with mammalian synenkephalin (Lecchi et al., 1997) whose amino acid sequence is 52% homologous with soricidin further supports this structure prediction by providing rationale for stabilization of the alpha/beta topology. The peptide architecture, based on topology homology with the Chinese scorpion (*Buthus martensi*) toxin BmBKTx1 (no sequence homology with soricidin) (Cai et al., 2004), shows a calcium-activated potassium ion channel blocker and a mechanism of paralysis similar to that displayed by this family of non-homologous scorpion neurotoxins.

Figure 14:
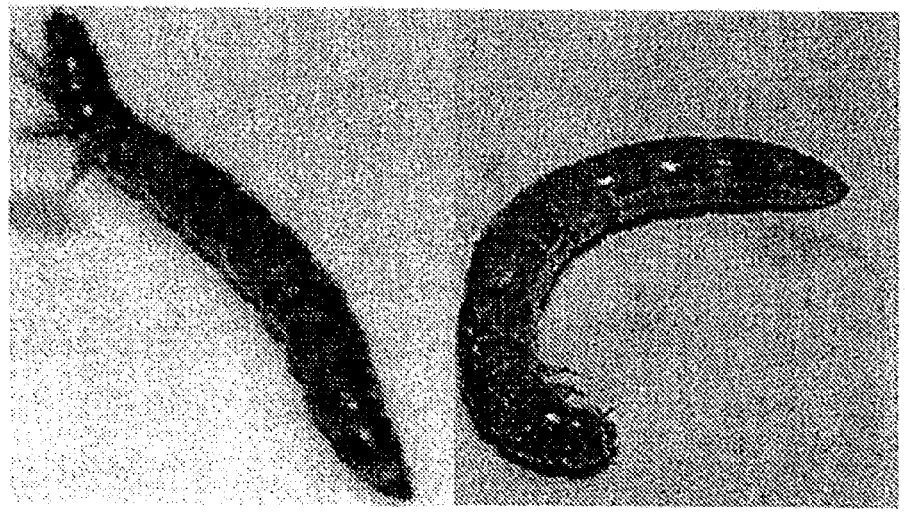
FIG. 14. Mealworms immediately post-injection (A) and with total paralysis (B).

Thus the invention includes a method of isolating and sequencing a paralytic shrew peptide by isolating the peptide as described in this application and sequencing the peptide. In one embodiment, the sequence of the isolated and purified shrew saliva peptide is shown in FIG. 1A (SEQ ID NO:1) and a derivative sequence is shown in FIG. 1B (SEQ ID NO:2) and the invention includes other derivatives of the sequence as described herein. Two examples of methods that are optionally used to isolate the protein are: i) size exclusion and ion exchange chromatography and ii) centrifugation through membranes with distinct molecular weight cut-offs: preferably 100,000, 10,000 and 3,000 Dalton molecular weight cut-off Centricons from Amicon. Other methods are also useful. The first method allows separation of the complexed active agent (very high molecular fractions) from where a free peptide of molecular weight 6000 would normally elute from the size exclusion chromatography column. The ion exchange chromatographic protocols employed a anion exchanger of a sodium phosphate buffer, neutral pH. The peptide is strongly bound to the complex (increased ionic strength does not dissociate it) and preferably is exposed to treatment with sodium dodecylsulfate (SDS) or with aqueous ethanol to dissociate it from the complex. Any short chain alcohol (preferably C1 to C6, more preferably C2 or C3) such as isopropyl alcohol, propanol or butanol may be used in place of ethanol. It appears that the bioactive peptide is kept complexed in the salivary gland until it is released as an active form in the saliva. The production of active peptide can be increased, for example, by first preparing a cold acetone precipitation (eg. a pH 7 phosphate buffered 10% (w/v) homogenate of the submaxilary gland) or other suitable precipitation solvent, dissolving the dried solid acetone precipitate (eg. in pH 7 phosphate buffer) and incubating (eg. at 37° C. for 20 minutes). This treatment increases the release of active peptide from the complex containing it. As well, the pure peptide can be isolated by preparative HPLC or other separation methods. The peptide isolate is reactive with Clellands reagent indicating the presence of sulfhydryl groups and the amino acid cysteine although it is reasonable to expect these to exist in disulfhydryl bonds. The peptide preparation also showed an absorbance at 280 nm indicating the presence of aromatic amino acids. In particular, the peptide preparation showed weak absorption at 280 nm, but stronger absorption at 260 nm, indicating phenylalanine but not tyrosine and tryptophan. FIG. 14 shows mealworms immediately post-injection and with total paralysis.

The peptide may be modified as described below to produce variants of the paralytic peptide with different paralytic potencies. Some variants that will be developed by this process will have the potential to behave as competitive inhibitors (e.g. antidotes) to paralysis developed in response to our peptide.

Peptides of the Invention

The invention provides an isolated PS peptide. The term "PS peptide" as used herein includes the peptides shown in FIG. 1A (SEQ ID NO:1) or FIG. 1B (SEQ ID NO:2), homologs, analogs, mimetics, fragments or derivatives of the PS peptide.

In one embodiment, the isolated PS peptide consists of 54 amino acid residues and has the sequence shown in FIG. 1A (SEQ ID NO:1) or the derivative shown in FIG. 1B (SEQ ID NO:2). In another embodiment, the PS peptide comprises sequences substantially identical to the above-noted peptides or comprising an obvious chemical equivalent thereof. It also includes peptide sequence plus or minus amino acids at the amino and/or carboxy terminus of the above-noted PS peptide sequences. In yet another embodiment, the invention includes fusion proteins, comprising the PS peptide, labeled PS peptides, analogs, homologs and variants thereof.

Within the context of the present invention, a peptide of the invention may include various structural forms of the primary PS peptide which retain biological activity. For example, a peptide of the invention may be in the form of acidic or basic salts or in neutral form. In addition, individual amino acid residues may be modified by oxidation or reduction.

In addition to the full-length amino acid sequence, the peptide of the present invention may also include truncations, analogs and homologs of the peptide and truncations thereof as described herein. Truncated peptides or fragments may comprise peptides of at least 5, 10, 15, 20, 25, 30, 35, 40, 45 or 50 amino acids or more amino acid residues of the sequence listed above. Useful fragments also include, for example, 50-54, 45-50, 45-52, 44-55, 42-54, 40-54, 35-45 or 25-35 amino acids. Useful fragments are capable of providing analgesia or neuromuscular blocking Amino acid nos. 42-54, 40-54, 38-54 and 45-54 are examples of useful fragments.

The invention further provides polypeptides comprising at least one functional domain or at least one antigenic determinant of a PS peptide.

Analogs of the protein of the invention and/or truncations thereof as described herein, may include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the peptides of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences of the invention. Amino acid insertions may consist of single amino acid residues or sequential amino acids ranging for example from 2 to 15 amino acids in length. For example, amino acid insertions may be used to destroy target sequences so that the peptide is no longer active. This procedure may be used to inhibit the activity of the peptide of the invention.

Deletions may consist of the removal of one or more amino acids, or discrete portions from the amino acid sequence of the PS peptide. The deleted amino acids may or may not be contiguous.

Analogs of a protein of the invention may be prepared by introducing mutations in the nucleotide sequence encoding the peptide. Mutations in nucleotide sequences constructed for expression of analogs of a protein of the invention must preserve the reading frame of the coding sequences. Furthermore, the mutations will preferably not create complementary regions that could hybridize to produce secondary mRNA structures such as loops or hairpins, which could adversely affect translation of the mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures may be employed to provide an altered gene having particular codons altered according to the substitution, deletion, or insertion required. Deletion or truncation of a peptide of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

In addition, analogs of a protein of the invention can be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). The peptides of the invention also include peptides having sequence identity to the PS peptide, mutated PS peptides and/or truncations thereof as described herein. Such peptides have amino acid sequences that correspond to nucleic acid sequences that hybridize under stringent hybridization conditions (see discussion of stringent hybridization conditions herein) with a probe used to obtain a peptide of the invention. Peptides having sequence identity will often have the regions which are characteristic of the protein.

Peptides preferably have an amino acid sequence with at least 70%, 80%, 90%, 95%, 96%, 97%, 98%, 99%, preferably 80-95% or more identity with the amino acid sequence of the PS peptide. The compound is optionally pharmaceutical grade purity (eg. for amino acids, this optionally means in excess of 99% purity, having a uniform crystalline structure, and white in color). Sequence identity is most preferably assessed by the BLAST version 2.1 program advanced search (parameters as above; Altschul, S. F., Gish, W., Miller, W., Myers, E. W. & Lipman, D. J. (1990) "Basic local alignment search tool." J. Mol. Biol. 215:403 410). BLAST is a series of programs that are available online from the National center for Biotechnology Information (NCBI) of the U.S. National Institutes of Health. The advanced blast search is set to default parameters. (i.e. Matrix BLOSUM62; Gap existence cost 11; Per residue gap cost 1; Lambda ratio 0.85 default).

The invention also contemplates isoforms of the peptides of the invention. An isoform contains the same number and kinds of amino acids as a peptide of the invention, but the isoform has a different three-dimensional molecular structure. The isoforms contemplated by the present invention are those having the same properties as a peptide of the invention as described herein.

The present invention also includes a protein of the invention conjugated with a selected protein, or a selectable marker protein to produce fusion proteins. For example, the cDNA sequence to the PS peptide can be inserted into a vector that contains a nucleotide sequence encoding another peptide (e.g. GST-glutathione succinyl transferase). The fusion protein is expressed and recovered from prokaryotic (e.g. bacterial or baculovirus) or eukaryotic cells. The fusion protein can then be purified by affinity chromatography based upon the fusion vector sequence and the PS peptide obtained by enzymatic cleavage of the fusion protein.

An alternative method of producing the protein is by using a poly-histidine tag. The cDNA sequence is designed to have a poly-histidine tag on the N-terminal end. The protein is expressed in prokaryotic or eukaryotic cells, and then easily isolated using a nickel-affinity column. The polyhistidine (usually 6 histidines) adsorbs strongly to the nickel attached to the affinity column while nothing else binds strongly. The 'his-tagged' peptide is isolated by washing the column with imidazole.

The proteins of the invention (including truncations, analogs, etc.) may be prepared using recombinant DNA methods. Accordingly, nucleic acid molecules of the present invention having a sequence that encodes a peptide of the invention are isolated using known technologies and are incorporated according to procedures known in the art into an appropriate expression vector that ensures good expression of the peptide. The cDNA is preferably obtained by Reverse Transcriptase-Polymerase Chain Reaction (RT-PCR). The technology comes as a kit form. One isolates the messenger RNA that encodes the peptide and then uses reverse transcriptase to convert all messengers in an extract of tissue to cDNA copies. One then amplifies the cloned DNA by standard PCR using a primer synthesized to match a segment of the peptide. The RACE technique is useful to obtain the full mRNA transcript since it codes for a series of peptides that are then cleaved after a bigger protein containing all of them is synthesized. Expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" means that the nucleic acid is linked to regulatory sequences in a manner that allows expression of the nucleic acid.

The invention therefore includes a recombinant expression vector of the invention containing a nucleic acid molecule of the invention, or a fragment thereof, and the necessary regulatory sequences for the transcription and translation of the inserted peptide-sequence. Suitable regulatory sequences are optionally derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native compound and/or its flanking regions.

The invention further provides a recombinant expression vector comprising a DNA nucleic acid molecule of the invention cloned into the expression vector in an antisense orientation. These vectors are useful experimental systems to study the peptides of the invention or its variants or to test antidotes. The peptides may or may not be toxic to the host cells. They are also useful to produce large amounts of the peptide. The vectors are particularly useful because insect-specific biological delivery agents (e.g. viruses) will provide immobilizing agents for specifically targeted insects. Viruses targeted against a specific insect pest are engineered to contain the gene fragment coding for the paralytic peptide along with expression regulatory sequences. The virus would target an insect species and then, during reproducing itself, also produce the peptide. Regulatory sequences operatively linked to the antisense nucleic acid can be chosen which direct the continuous expression of the antisense RNA molecule.

The recombinant expression vectors of the invention may also contain a selectable marker gene that facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. These cells are useful experimental systems. Accordingly, the invention includes a host cell comprising a recombinant expression vector of the invention. The term "transformed host cell" is intended to include prokaryotic and eukaryotic cells which have been transformed or transfected with a recombinant expression vector of the invention. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the peptides of the invention may be expressed in bacterial cells such as *E. coli, Pseudomonas, Bacillus subtillus*, insect cells (using baculovirus), yeast cells or mammalian cells. Other suitable host cells can be found in Goeddel, Gene Expression Technology: Methods in Enzymology 185, Academic Press, San Diego, Calif. (1991).

As an example, to produce PS peptides recombinantly, for example, *E. coli* can be used using the T7 RNA polymerase/promoter system using two plasmids or by labeling of plasmid-encoded proteins, or by expression by infection with M13 Phage mGPI-2. *E. coli* vectors can also be used with Phage lambda regulatory sequences, by fusion protein vectors (e.g. lacZ and trpE), by maltose-binding protein fusions, and by glutathione-S-transferase fusion proteins.

Alternatively, a PS peptide can be expressed in insect cells using baculoviral vectors, or in mammalian cells using vaccinia virus. For expression in mammalian cells, the cDNA sequence may be ligated to heterologous promoters and introduced into cells, such as COS cells to achieve transient or long-term expression. The stable integration of the chimeric gene construct may be maintained in mammalian cells by biochemical selection, such as neomycin and mycophenolic acid.

The PS DNA sequence can be altered using procedures such as restriction enzyme digestion, fill-in with DNA polymerase, deletion by exonuclease, extension by terminal deoxynucleotide transferase, ligation of synthetic or cloned DNA sequences, site-directed sequence alteration with the use of specific oligonucleotides together with PCR. For example, one to five or five to ten amino acids or more may be removed or mutated.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation.

The endogenous PS gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

PS peptides may also be isolated from cells or tissues, including mammalian cells or tissues, in which the peptide is normally expressed.

The protein may be purified by conventional purification methods known to those in the art, such as chromatography methods, high performance liquid chromatography methods or precipitation.

For example, an anti-PS antibody (as described below) may be used to isolate a PS peptide, which is then purified by standard methods.

The peptides of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

Peptide Mimetics

The present invention also includes peptide mimetics of PS. "Peptide mimetics" are structures which serve as substitutes for peptides in interactions between molecules (See Morgan et al (1989), Ann. Reports Med. Chem. 24:243-252 for a review). Peptide mimetics include synthetic structures which optionally contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics are designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention are also useful to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds is evaluated using assays similar to those described herein. Information about structure-activity relationships is obtained from co-crystallization studies. In these studies, a peptide with a desired activity is crystallized in association with a target molecule, and the X-ray structure of the complex is determined. The structure is then optionally compared to the structure of the target molecule in its native state, and information from such a comparison is useful to design compounds expected to possess.

Therapeutic and Cosmetic Methods

The paralytic agent is useful for the neuromuscular disorder market including the well publicized cosmetic applications of neuromuscular blockers. (For a discussion of the use of Botox for immobilization of facial muscles and treatment of wrinkles, see: Fagien, S. 1999. Plast Reconstr Surg 103: 701-713; Carruthers, J, & Carruthers, A. 1998. Dermatol Surg 24: 1244-1247). Therapeutic applications of neuromuscular blockers such as relief of migraine, myofacial and other types of pain (i.e., analgesic activity) have recently been added to existing medical uses that include muscle tremors and neuromuscular diseases. New uses are steadily emerging including the cosmetic application of wrinkle reduction and, more recently, treatment of excessive sweating (also called hyperhidrosis; Blaheta, H J, Vollert, B, Zuder, D, & Rassner, G. 2002. Dermatol. Surg. 28:666-671; Naumann, M & Hamm, H. 2002. Br. J. Surg. 89: 259-261).

Accordingly, in one embodiment, the present invention provides a method of blocking neuronal activity comprising administering an effective amount of PS peptide such as SEQ ID NO:1 or SEQ ID NO:2 or the other compounds described in this application to an animal in need thereof. The present invention also provides a use of an effective amount of a PS peptide as a neuromuscular blocker. The present invention further provides a use of an effective amount of a PS peptide in the manufacture of a medicament for blocking neuronal activity or providing analgesia.

Another embodiment of the invention provides a method of wound healing comprising administering an effective amount of PS peptide to an animal in need thereof. The present invention further provides a use of the PS peptide in wound healing, for example by providing analgesia For example, dressings can be embedded with the PS peptide or gels containing the PS peptide can be applied to dressing, to behave as a long-lasting, local analgesic to wounds.

The phrase "substance that can block neuromuscular activity" as used herein includes all the peptides of the invention described herein that block neuromuscular activity temporarily or permanently, including but not limited to pain receptors (eg. a nociceptor, which is a peripheral nerve organ or mechanism for the reception and transmission of painful or injurious stimuli).

The term "effective amount" as used herein means an amount effective and at dosages and for periods of time necessary to achieve the desired result (e.g., blocking neuromuscular activity).

The term "animal" as used herein includes all members of the animal kingdom and is preferably mammalian, such as human. Administering a PS peptide or substance to an animal includes both in vivo and ex vivo administrations.

The term "a cell" as used herein includes a single cell as well as a plurality or population of cells. Administering a PS peptide or substance to a cell includes both in vitro and in vivo administrations.

The phrase "block neuromuscular activity" as used herein means that the substance can result in a decrease in neuromuscular activity as compared to a neuromuscular activity in the absence of the substance.

Blocking neuromuscular activity is useful for an analgesic in treating diseases such as migraine, tremors, neuromuscular disease, excess sweating and wrinkles. Accordingly, in a specific embodiment, the present invention relates to a method of treating the aforementioned diseases comprising administering an effective amount of a PS substance to an animal in need thereof. The present invention also provides a use of an effective amount of a substance that can block neuromuscular activity or provide analgesia. The present invention further provides a use of an effective amount of a PS substance that can inhibit neuromuscular function to prepare a medicament to treat the aforementioned diseases.

Figure 16:
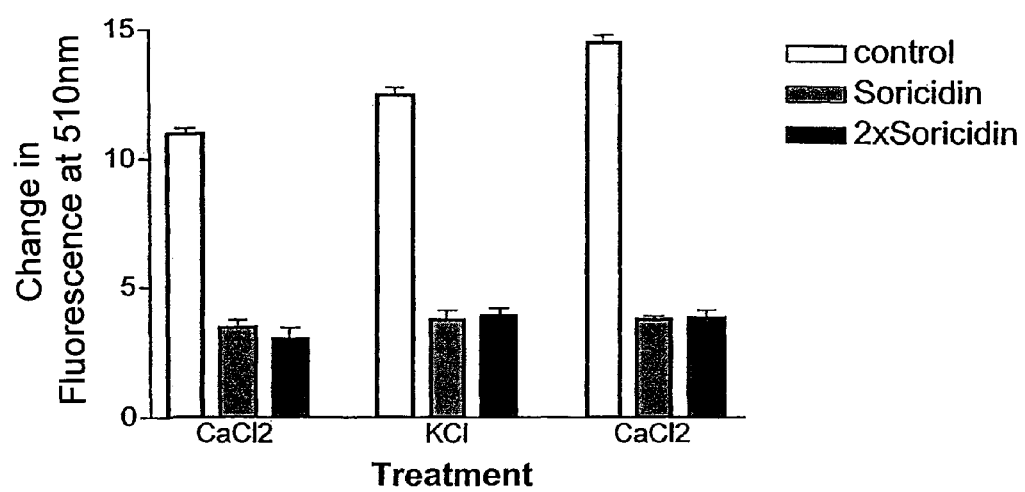
FIG. 16. The increased fluorescence due to calcium ion uptake by ovarian carcinoma cell line OV-2008 and subsequent formation of the FURA/$Ca^{+2}$ in the absence (control) and presence of the paralytic shrew peptide soricidin after initial treatment with calcium chloride (to a final concentration of 2.5 mM), potassium chloride (to 20 mM) and a final calcium chloride (to a final concentration of 5.0 mM) treatments.

Soricidin strongly inhibits calcium uptake in cancer cells, such as ovarian carcinoma cell line OV-2008 (FIG. 16). The major calcium uptake channel expressed in carcinomas of breast, thyroid, colon prostate and ovarian carcinomas is CaT1 (TRPV6) (Zhuang et al. 2002). This calcium channel is not expressed in normal ovarian tissue but is at lower levels in the other tissues listed. Carcinomas of all of the listed tissues show increased TRPV6 expression (den Dekker et al., 2003). The expression of this calcium channel correlates with tumour grade in prostate cancer and is useful as a target for novel therapy (Peng et al., 2001). Expression of the calcium channel is both co-temporal with and a marker for tumour progression (den Dekker et al., 2003). Soricidin and soricidin derivatives, by inhibiting calcium uptake, inhibit this calcium channel and disrupt intracellular calcium essential for proliferation of normal and cancerous cells. Therefore, the invention includes the use of soricidin and soricidin derivatives, as described in this application, for reducing cell proliferation and preventing and/or treating tumours and cancer in animals, particularly mammals (e.g. humans) by administration of soricidin or a soricidin derivative to the animal.

Figure 17:
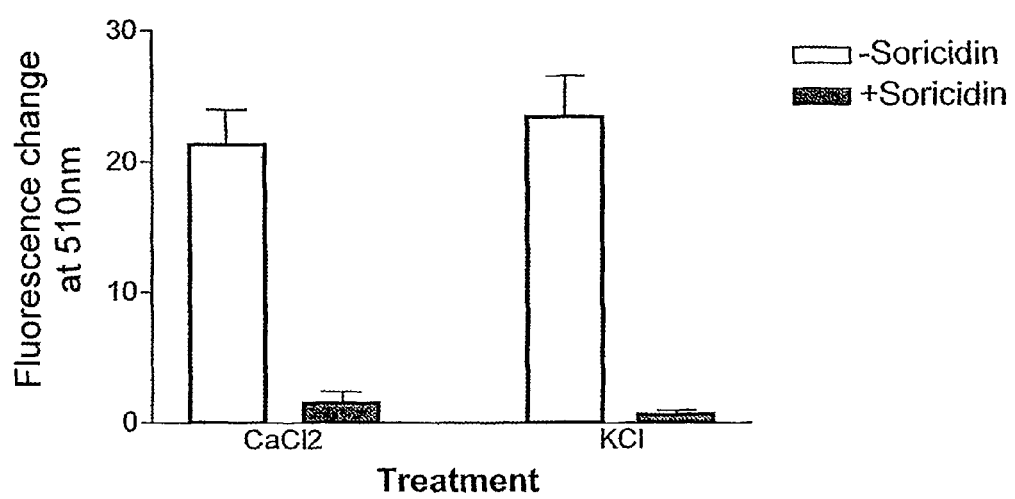
FIG. 17. The increased fluorescence due to calcium ion uptake by insect nerve tissue and subsequent formation of the FURA/$Ca^{+2}$ in the absence (control) and presence of the paralytic shrew peptide soricidin after a challenge with calcium chloride (to a final concentration of 2.5 mM) and potassium chloride (to 20 mM).

Soricidin inhibits calcium uptake in insect neural tissue (FIG. 17). Such uptake has been associated with sensory signaling processes and nociception in invertebrates (Montel, 2003). Therefore, the invention also includes the use of soricidin and soricidin derivatives, as described in this application, for reducing noiception in animals, particularly mammals (eg. humans) by administration of soricidin or a soricidin derivative to the animal.

As used herein, and as well understood in the art, "to treat" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease or disorder, preventing spread of disease or disorder, delay or slowing of disease or disorder progression, amelioration or palliation of the disease or disorder state, and remission (whether partial or total), whether detectable or undetectable. "Treatment" can also mean prolonging survival as compared to expected survival if not receiving treatment.

Pharmaceutical and Cosmetic Compositions

The nucleic acids encoding the PS peptides, for example, the peptides show in FIGS. 1A and 1B, are optionally formulated into a pharmaceutical composition for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Administration of a therapeutically active amount of pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

The polypeptide of the invention is preferably combined with other components such as a carrier in a composition such as a pharmaceutical composition or cosmetic composition. The compositions are useful when administered in methods of medical treatment, prevention, or diagnosis of a disease, disorder or abnormal physical state. For example, it may be administered as a neuromuscular blocker. They are useful for treatment of migraine, myofacial and other types of pain (analgesic function), muscle tremors and neuromuscular diseases, excessive sweating and wrinkles. They are also useful for wound healing by action as a local analgesic.

The pharmaceutical compositions can be administered to humans or animals by a variety of methods including, but not restricted to topical administration, oral administration, aerosol administration, intratracheal instillation, intraperitoneal injection, injection into the cerebrospinal fluid, intravenous injection and subcutaneous injection. Dosages to be administered depend on patient needs, on the desired effect and on the chosen route of administration. For example, the pharmaceutical compositions can be on a bandage, which is used for wound healing by acting as an analgesic. Nucleic acid molecules and polypeptides may be introduced into cells using in vivo delivery vehicles such as liposomes. They may also be introduced into these cells using physical techniques such as microinjection and electroporation or chemical methods such as coprecipitation or using liposomes.

The pharmaceutical compositions are prepared by known methods for the preparation of pharmaceutically acceptable compositions which can be administered to patients, and such that an effective quantity of the nucleic acid molecule or polypeptide is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA) or Handbook of Pharmaceutical Additives (compiled by Michael and Irene Ash, Gower Publishing Limited, Aldershot, England (1995). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

On this basis, the pharmaceutical compositions optionally includes an active compound or substance, such as a peptide or nucleic acid molecule, in association with one or more pharmaceutically acceptable vehicles or diluents, and contained in buffered solutions with a suitable pH and isoosmotic with the physiological fluids. The methods of combining the active molecules with the vehicles or combining them with diluents is well known to those skilled in the art. The composition optionally includes a targeting agent for the transport of the active compound to specified sites within tissue.

Preparation of Antibodies

Antibodies to the peptide are useful to identify receptors and will find use in development of diagnostic tests. Some neuromuscular conditions result from malfunction of the peptide target. Detecting the target receptor molecules and determining their density on the surface of the cell, or their location on the cell surface is useful in diagnostics. This can be done with antibody treatment after peptide administration and then secondary detection of the antibody/peptide complexes as in the general ELISA protocol. Any method of labeling the peptide that would report on receptor density/location would be useful (e.g. radioactively labelled peptide or fluorescently tagged peptide). Once the peptide and its receptor are characterized as to how the effect is solicited, the PS peptide or variants are used to test how the target works in other tissues or animals or people. A variant or damaged receptor/target to the PS peptide or variant would not act in a manner that is identical to the characterized 'normal' target. The invention includes an isolated antibody immunoreactive with a polypeptide of the invention. Antibodies are preferably generated against epitopes of the sequence. The antibody is optionally labeled with a detectable marker or unlabeled. The antibody is typically a monoclonal antibody or a polyclonal antibody. Such antibodies are employed to screen organisms. The antibodies are also valuable for immuno-purification of polypeptides from crude extracts. For example, one may contact a biological sample with the antibody under conditions allowing the formation of an immunological complex between the antibody and a polypeptide recognized by the antibody and detecting the presence or absence of the immunological complex whereby the presence of the peptide of the invention or a similar peptide is detected in the sample. The invention also includes compositions preferably including the antibody, a medium suitable for the formation of an immunological complex between the antibody and a polypeptide recognized by the antibody and a reagent capable of detecting the immunological complex to ascertain the presence of the peptide of the invention or a similar polypeptide.

To recognize the peptide of the invention, one may generate antibodies against a range of unique epitopes throughout the molecule.

Monoclonal and polyclonal antibodies are prepared according to the description in this application and techniques known in the art. For examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705 that are incorporated by reference in their entirety. Examples of the preparation and uses of polyclonal antibodies are disclosed in U.S. Pat. Nos. 5,512,282, 4,828,985, 5,225,331 and 5,124,147 which are incorporated by reference in their entirety.

The term "antibody" as used herein to includes fragments thereof which also specifically react with a PS peptide or fragments thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules include, for example, the antigen binding domain from an antibody of a mouse, rat, or other species, with human constant regions. Conventional methods are useful to make chimeric antibodies containing the immunoglobulin variable region which recognizes the PS peptide antigens of the invention (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules are made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, such as, but not limited to, single-chain Fv monoclonal antibodies reactive against the peptides of the invention may also be generated by screening expression libraries encoding immunoglobulin genes, or portions thereof, expressed in bacteria with peptides produced from the nucleic acid molecules of PS peptides. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

The invention also includes methods of using the antibodies, such as in detection of receptors that bind to the peptide of the invention. For example, the invention includes a method for detecting the presence of a peptide of the invention by: a) contacting a sample containing one or more peptides with an antibody of the invention under conditions suitable for the binding of the antibody to peptides with which it is specifically reactive; b) separating unbound peptides from the antibody; and c) detecting antibody which remains bound to one or more of the peptides in the sample.

Research Tool

The peptide and its derivatives are useful in research protocols to explore the neuromuscular junction and ion channels. The ability to selectively alter certain ion channels or classes of ion channels provides another tool with which to perturb the neuromuscular junction in a predictable manner. This identifies the role of susceptible peptide targets in neuromuscular functions and processes. The invention includes a method of determining the response of an ion channel to a paralytic peptide comprising contacting a channel or cells comprising a channel with soricidin or a derivative thereof and determining whether the channels transportions or whether ion transport (e.g. $Ca^{2+}$ and/or $K^+$) has been reduced.

EXAMPLES

The following examples are illustrative embodiments and do not limit the scope of the invention.

Example 1

Isolation and Purification of the Shrew Saliva Peptide from the Submaxilary Saliva Glands of the Shrew (*Blaring Brevicauda*)

Tissue Processing

The left and right submaxilary glands (ranging between 100 and 200 mg total weight) are dissected and placed into liquid nitrogen to flash freeze them. The tissue is crushed and powdered under liquid nitrogen. The tissue powder is quickly transferred to weighed receptacle and the weight of the transferred tissue powder is determined. The tissue is then homogenized in 50 mM potassium phosphate buffer, pH 7.0 to provide a 20% weight-to-volume (2 g/100 mL) homogenate. The homogenate is centrifuged at 12,000×g at 4° C. for 15 minutes to pellet the cell debris. The supernatant is removed.

If the glands are not to be used immediately they are flash frozen in liquid nitrogen and stored at −80° C. or lower until processing.

Isolation of the Peptide

The methods to isolate and purify the shrew saliva protein include: i) size exclusion and ion exchange chromatography (see FIGS. 2 and 3) and ii) centrifugation with distinct molecular weight cut-offs: preferably 100,000, 10,000 and 3,000 molecular weight cut-off Centricons from Amicon. The first method allows separation of the complexed active agent (very high molecular fractions) from where a free peptide of molecular weight 6000 would normally elute from the size exclusion chromatography column. The ion exchange chromatographic protocols employed a anion exchanger of a sodium phosphate buffer, neutral pH. The peptide is strongly bound to the complex (increased ionic strength does not dissociate it) and preferably is exposed to treatment with sodium dodecylsulfate (SDS) or with aqueous ethanol to dissociate it from the complex. Any short chain alcohol (preferably C1 to C6, more preferably C2 or C3) such as isopropyl alcohol, propanol or butanol may be used in place of ethanol. Warming the crude extract at 40° C. for 20 minutes increases the amount of isolatable peptide. It appears that the bioactive peptide is kept complexed in the salivary gland until it is released as an active form in the saliva. The peptide isolate is weakly reactive with Clellands reagent indicating the presence of sulfhydryl groups and the amino acid cysteine although it is reasonable to expect these to exist in disulfhydryl bonds. The peptide preparation also showed a weak absorbance at 280 nm and a strong absorbance at 260 nm indicating the presence of phenylalanine, but not tryptophan and tyrosine.

The size exclusion method can also include a precipitation step of the soluble proteins with cold acetone (−20° C. or −80° C.; 10:1 v/v acetone: homogenate), which also precipitates the larger molecular weight proteins. This acetone precipitation step can be done before or after size-fractionation. The acetone precipitate is air dried rapidly and is active for long period of time (Ellis S & Krayer 0 (1955) J Pharm Exper Therapeutics 114: 127-137). The precipitate (~50 mg) is dissolved in about 1 mL of 25 mM potassium phosphate buffer and isolated by HPLC immediately or first incubated at 40° C. before HPLC isolation.

High Pressure Liquid Chromatographic Isolation.

A way to isolate the peptide once the acetone precipitate is re-dissolved is reversed phase HPLC. A Phenomenex Jupiter C-18 column, 250×4.6 mm, 5 u at 20-25° C. and a gradient elution from 10% (v/v) acetonitrile: 90% (v.v) water to 60% acetonitrile: 40% water are used over 30 minutes and a flow rate of 1.0 mL/min. All solvents contain 0.1% (v/v) trifluoroacetic acid (TFA). This provide the elution profile shown in FIG. 4.

The active fraction of this first HPLC set is that peak eluting at about 14.7 minutes. This peak is collected (See FIG. 4, bar on 'time axis'). This material is lyophylized overnight to remove solvents and TFA.

Figure 5:
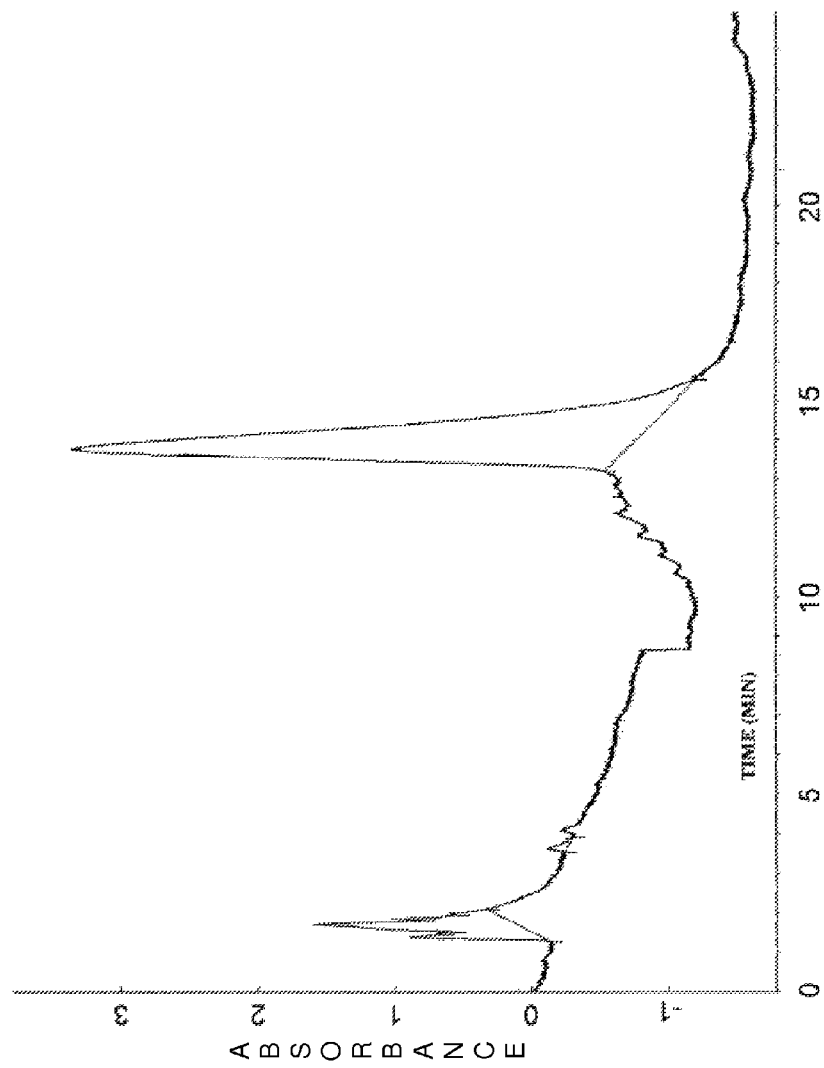
FIG. 5. Second HPLC elution profile of active fraction.

The residue containing the main peptide of interest and 2 to 3 minor other proteins is dissolved in a minimum volume of 25 mM potassium phosphate buffer. The solubilized peptide is purified under another HPLC protocol. A Phenomenex Jupiter C-18 column, 250×4.6 mm, 5 u at 20-25° C. and a gradient elution from 10% (v/v) acetonitrile: 90% (v.v) water to 60% acetonitrile: 40% water is used over 40 minutes and a flow rate of 2.3 mL/min. All solvents contain 0.1% (v/v) trifluoroacetic acid (TFA). This provides the elution profile shown in (See FIG. HPLC 02) with peptide eluting at 13.76 min: the collected eluant shown by the solid bar on the 'time axis' is pure peptide. This material is lyophilized removing the solvents and the TFA. This material is pure peptide by HPLC (FIG. 5), by SDS-PAGE (FIGS. 6 and 7) and by CE (FIGS. 8 and 9).

Capillary Electrophoresis

Purified shrew saliva peptide (dissolved in 25 mM potassium phosphate buffer, pH 7.0) was subjected to capillary electrophoresis using Beckman Coulter P/ACE Capillary Electrophoresis System in a 60 cm fused silica column ((75 um internal diameter, 375 um outer diameter) with sodium borate buffer (1 Molar, run buffer) thermostated to 25° C. The voltage regime was a 0.17 minute ramp to 30,000 volts for 20 minutes at normal polarity. The injection pressure was 0.5 pounds per square inch for 10.0 seconds providing a sample volume of approximately 5 nL (nanoliters)).

Figure 8:
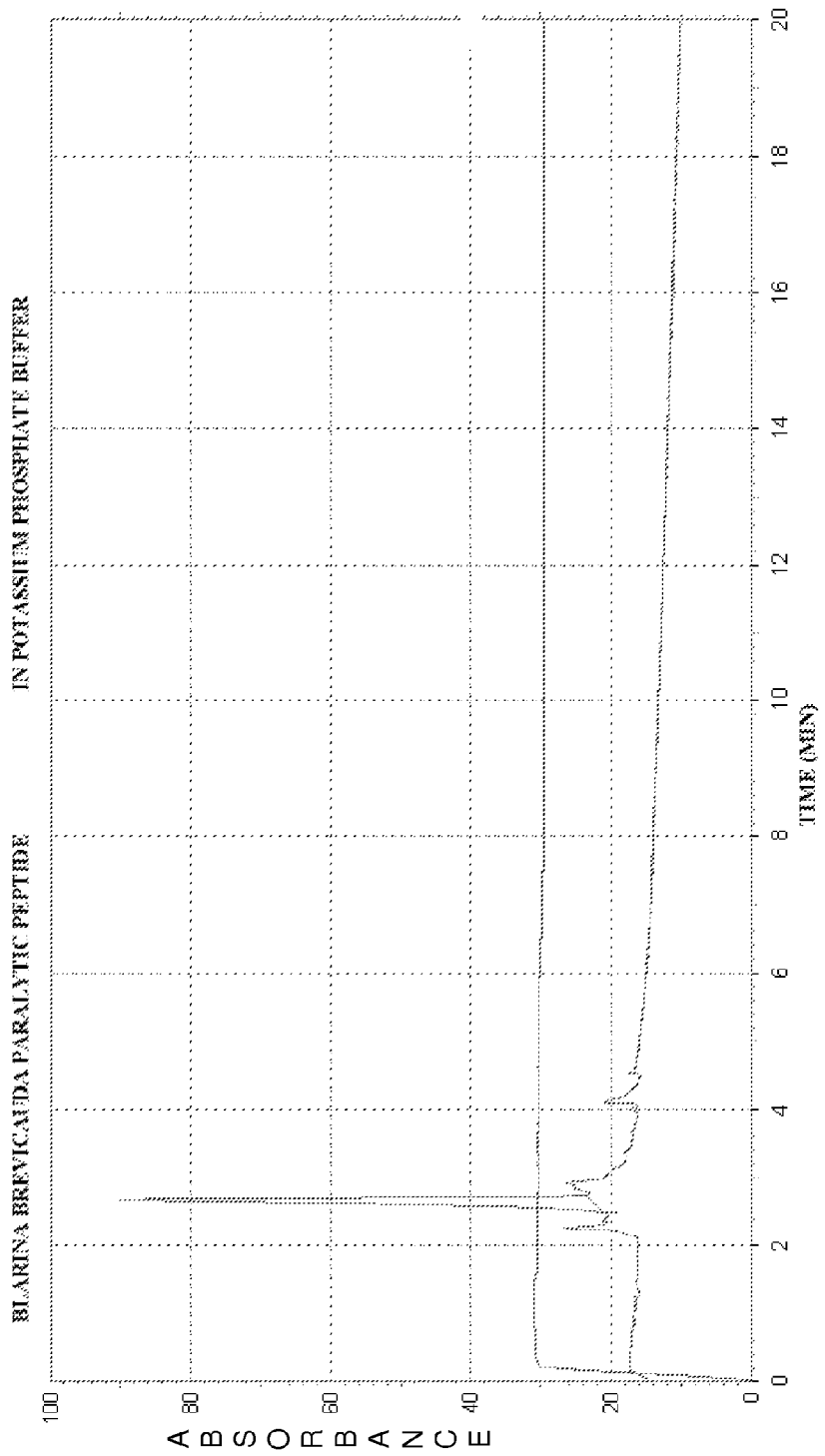
FIG. 8. Capillary electrophoretogram of the isolated and purified shrew saliva peptide in sodium borate buffer.
Figure 9:
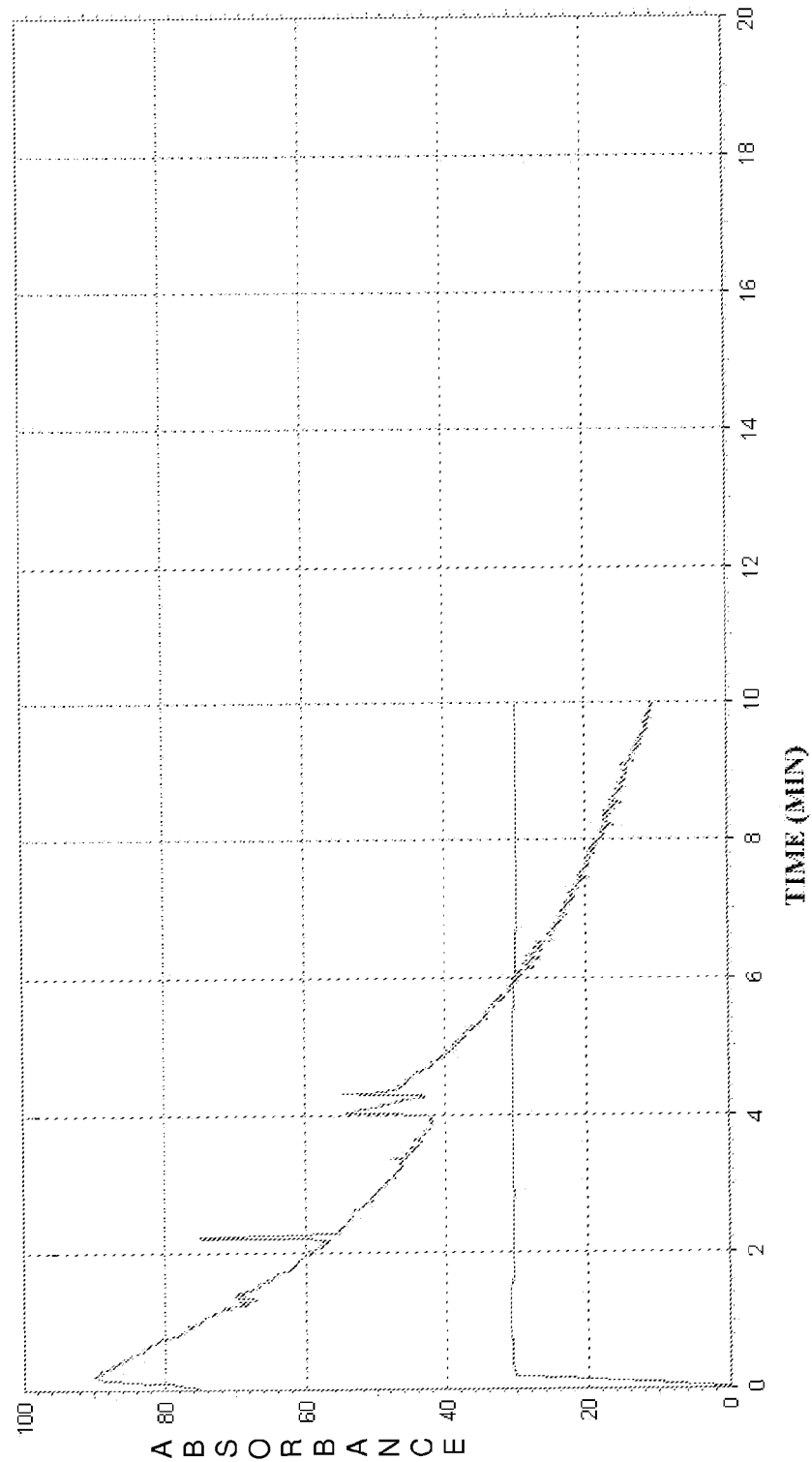
FIG. 9. Capillary electrophoretogram of the isolated and purified shrew saliva peptide.

FIG. 8 shows the electrophoretogram of the purified peptide in buffer and had an elution time of 2.67 minutes. FIG. 9 shows an identical electrophoretic run of the 25 mM potassium phosphate buffer. This peak showed an identical uv-spectrum as that obtained with a standard spectrophotometer (see below).

Electronic Spectrum

Figure 10:
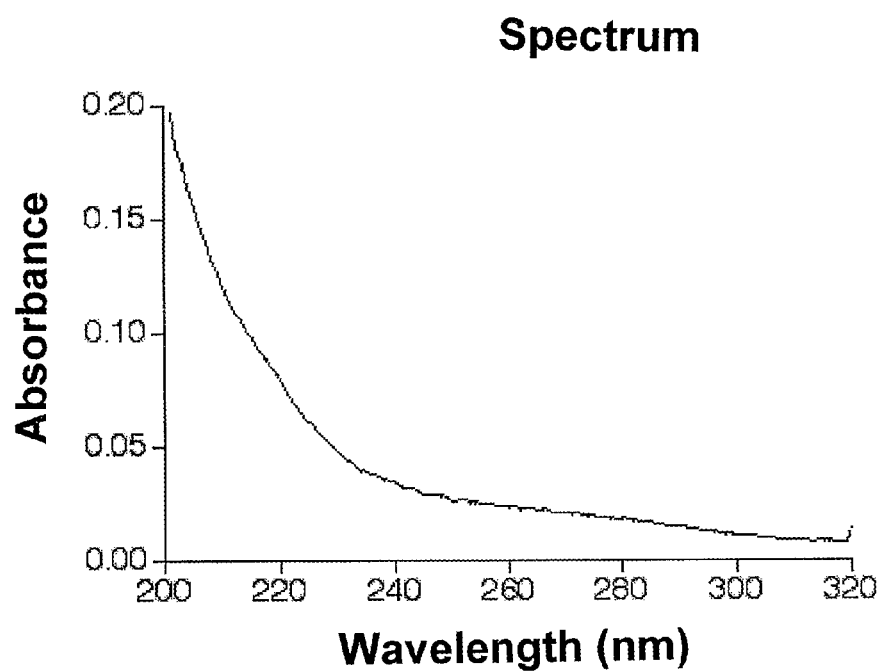
FIG. 10. Ultra-violet spectrum of the isolated and purified shrew saliva peptide.

Purified peptide was dissolved in 50 mM potassium phosphate, pH 7.0 and its ultra-violet spectrum measured (FIG. 10). The spectrum showed no absorption in the 280 nm range and thus indicated that the amino acids tryptophan and tyrosine were not present in the peptide. The shoulder centred about 260 nm indicated the presence of the amino acid phenylalanine while the low absorption indicated only a small amount of the amino acid present in the peptide. Subsequent amino acid sequencing of the peptide was consistent with this as there was no tryptophan or tyrosine and only one phenylalanine residue detected.

Post-translational Modification

Many salivary proteins are modified post-translationally by glycation but the isolated and purified shrew saliva peptide is not a glycoprotein produced by such a process. Shrew saliva peptide does not have carbohydrates attached covalently to its structure.

SDS-PAGE

Figure 6:
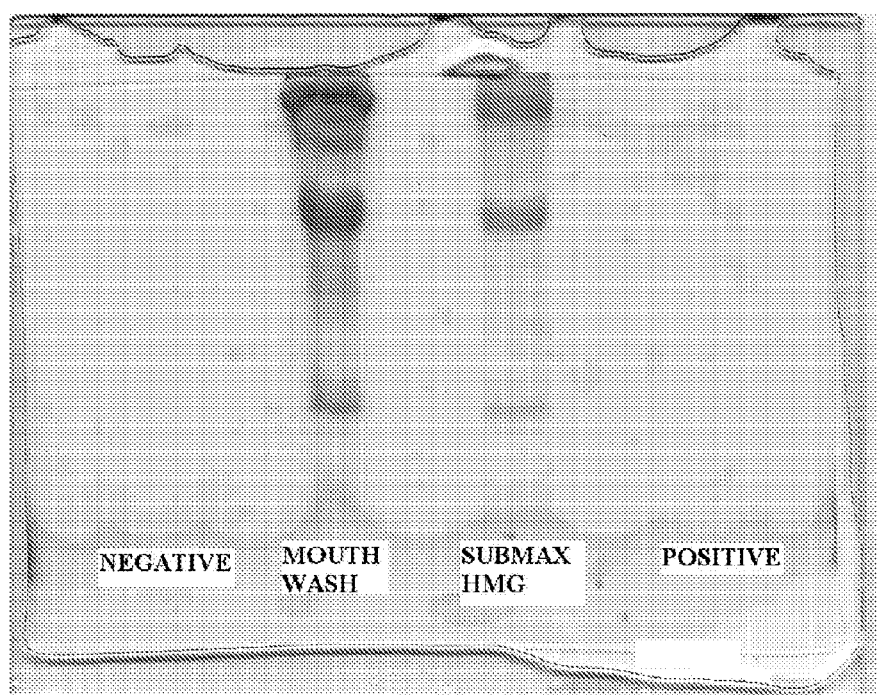
FIG. 6. SDS-PAGE gel of both buccal saliva and submaxilary homogenate stained for glycoproteins.
Figure 7:
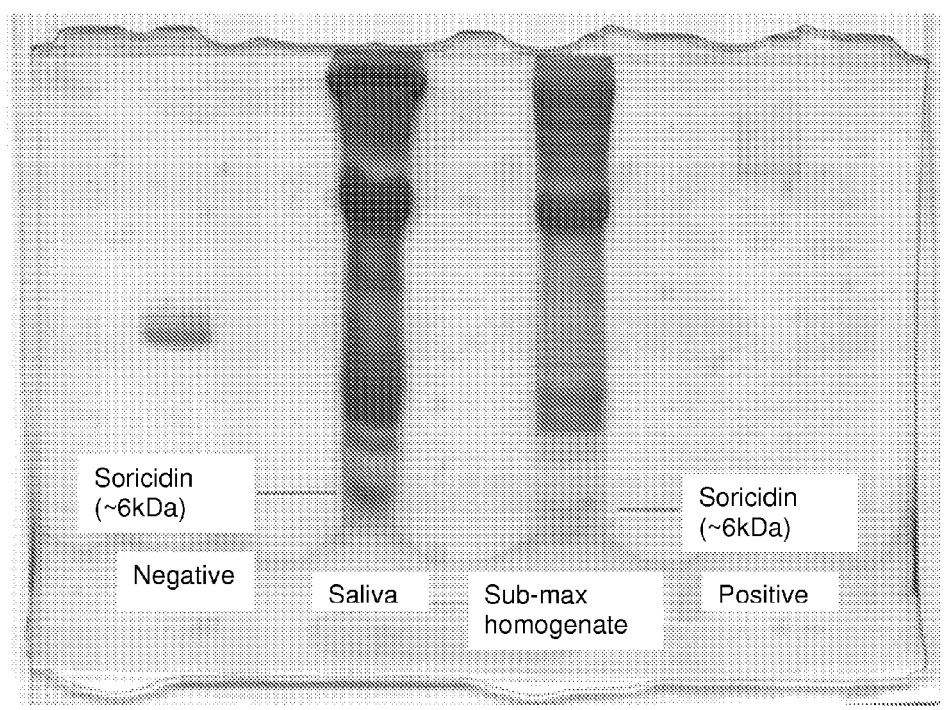
FIG. 7. SDS-PAGE gel Coomassie stain of both buccal saliva and submaxilary homogenate.

FIG. 6 shows an SDS-PAGE (15% acrylamide) gel of both buccal saliva (mouth wash) and sub-maxillary homogenate along with internal standards of a non-glycosylated and a glycosylated protein. FIG. 7 shows a protein stain (Coomassie) after the glycostaining was complete and is the same gel restained with Coomassie. Shrew saliva peptide appears at as the most mobile of the proteinaceous components (lowest stained, diffuse band) and did not react positively to the glycostain as did other proteins in these biological fluids at larger molecular weight.

Example 2

Amino Acid Sequence

The purified peptide was subjected to N-terminal sequencing using the Edman sequential degradation to obtain the sequence shown in FIG. 1A. Mass spectroscopy/mass spectroscopy (ms/ms) was also used to confirm portions of the sequence. The sequences in FIG. 1A, the derivative in FIG. 1B and other derivatives are useful peptides.

Molecular Ion of the Purified Peptide

Figure 11:
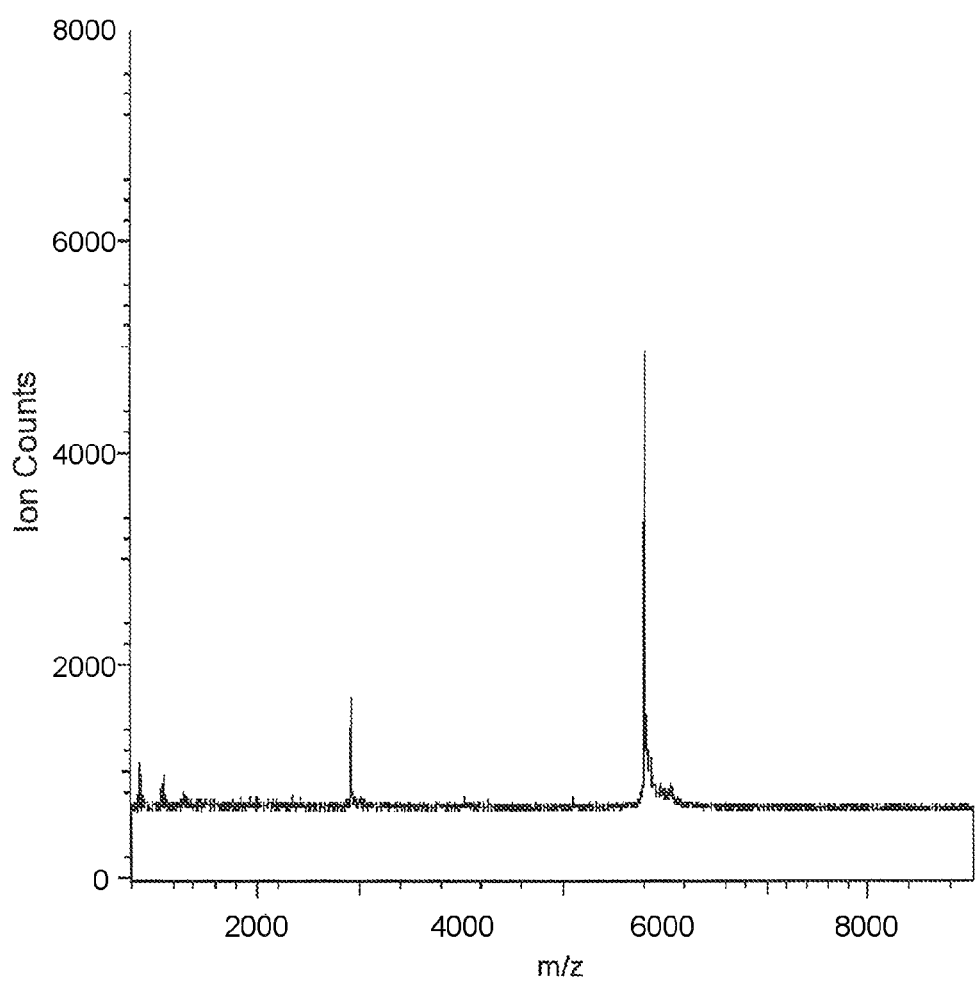
FIG. 11. MALDI-TOF mass spectrum of the isolated and purified shrew saliva peptide.

The molecular mass of isolated and purified shrew saliva peptide (Bruker Reflex III, MALDI-TOF, Linear mode, HCCA matrix, two layer method) provided a molecular cation (MH+) of 5805.8 Daltons and thus a molecular mass (M) of 5804.8 Daltons. (See FIG. 11)

Tryptic Digest Peptide Mass Map

Figure 12:
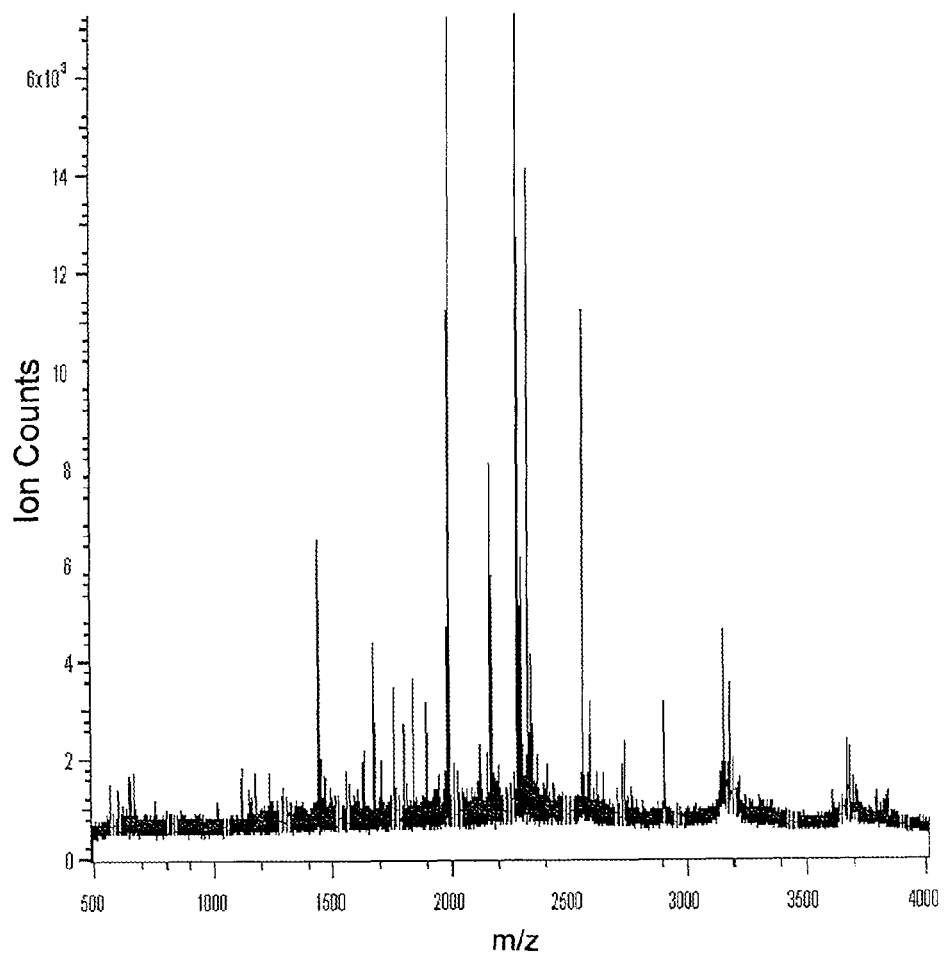
FIG. 12. Peptide mass mapping of tryptic peptides of the isolated and purified shrew saliva peptide.
Figure 13:
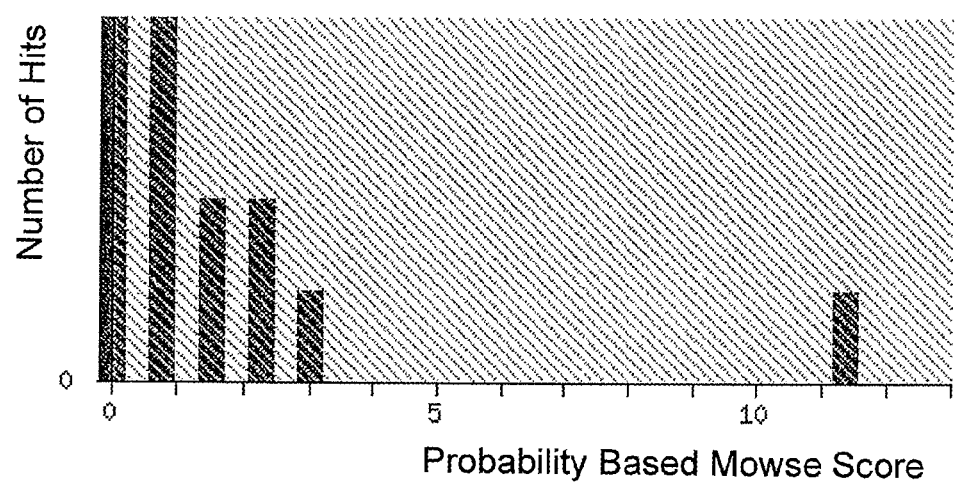
FIG. 13. MASCOT searching results of the MS/MS data from HPLC-ESI-Q-TOF analysis.

The tryptic digest followed by peptide mass mapping by MALDI-TOF provided the mass spectrogram presented in FIG. 12. This digestion mass map is absolutely distinctive of isolated and purified shrew saliva peptide. There were no matches of this mass map in and public database using the MASCOT searching (FIG. 13) (Perkins et al. 1999. Electrophoresis, 20(18) 3551-3567).

Theoretical Isoelectric Points and Mass

The theoretical isoelectric point and mass of the isolated and purified shrew saliva protein can be calculated. The theoretical isoelectric point is 4.60. The peptide mass was determined to be 5804.8 by mass spectrometry. The sequence above gives a theoretical mass of 5806 if the six cysteine residues are connected in 3 sulfhydryl bonds.

Example 3

Bioassay

The invention includes a bioassay that shows that paralytic saliva administered to the mealworm can keep it alive for at least 7 days. FIG. 14 shows mealworms immediately postinjection and with total paralysis. Other insects are also useful in the bioassay.

Example 4

Toxicity

Figure 15:
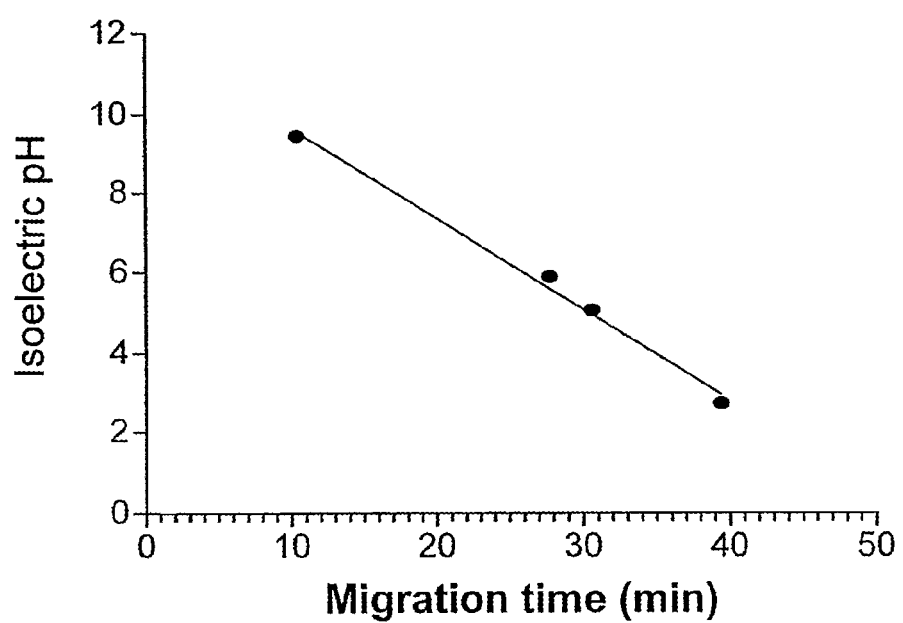
FIG. 15. Migration time vs isoelectric pH of Beckman-Coulter pI standard proteins.

Isoelectric pH of Soricidin:

The isoelectric pH of the shrew peptide soricidin was determined after calibration of the Beckmann-Coulter P/ACE MDQ Capillary Electrophoresis System with proteins of known isoelectric pH (2.75, 5.10, 5.90 and 9.45) and then co-isoelectric focusing of the standards with soricidin. FIG. 15 shows the linear correlation (pI=11.94-0.2281t) of migration times and the protein standards. The soricidin migration time (33.9 min) provided a pI of 4.20.

Soricidin Inhibits Calcium Ion Uptake a) Human Ovarian Carcinoma Cell Cultures

A human ovarian carcinoma cell line (OV 2008) was grown in MegaCell supplemented (Sigma Aldrich Chemical Co.) with 3% fetal calf serum (v/v), L-glutamine (584 mg/500 mL), and antibiotics penicillin and streptomycin (50 ug/ml) at 37° C. and in a humidified 5% carbon dioxide atmosphere. After confluence, the cells were harvested by incubation with Trypsin EDTA solution low in calcium and magnesium Dulbecco phosphate buffered saline (DPBS) at 37° C. and gentle shaking to detach them from the culture flask surface. After centrifugation and washing in the calcium-depleted medium, cells were incubated with 5 uM FURA 2AM for 60 minutes to internalize this calcium sensitive fluorophore. After centrifuging and washing twice with DPBS, cells were allowed to de-esterify the FURA 2AM for 30 minutes at 37° C., activating the calcium-sensitive FURA. Cells were then incubated with aliquots of a solution of pure soricidin. Fluorescent analysis used excitation at 340 nm and emission at a wavelength of 510 nm. After recording the baseline fluorescence of the cells, a bolus of calcium chloride (to final concentration of 2.5 mM) was delivered to the cell suspension and the fluorescence remeasured. After recording the fluorescence, the sample was treated with a bolus of potassium chloride (final concentration 20 mM) to activate any voltage gated calcium channels. Finally, the cells were treated with another bolus of calcium chlorine raising the calcium ion concentration to 5.0 mM. The control situation was no treatment with soricidin peptide but with identical other treatments.

Normal ovarian cultures do not express calcium ion channels but ovarian carcinoma cells display a highly selective calcium channel, CaT1 (also called CaT-L, ECaC2 and more recently TRPV6) (Zhuang et al., 2002). This transient receptor potential (TRP) calcium channel was blocked by soricidin. FIG. 16 illustrates a) soricidin inhibits calcium uptake by the OV-2008 cell line;

b) the inhibitory effect was saturated at the soricidin doses used as increases in the amount used caused no additional inhibition of calcium uptake;

c) the small increase in calcium uptake in response to potassium ion challenge in the control situation is eliminated by soricidin treatment showing that either a small population of voltage-gated calcium ion channels on these cells is inhibited or a potassium channel is also inhibited.

b) Excised Insect Nerve Tissue

Central nerve pairs running along 5 body segments (including ganglia) were excised from flour beetle larvae (meal worms) and suspended in buffered invertebrate saline containing FURA 2AM. After 60 minutes, the nerve tissue was removed from this solution, briefly washed in buffered saline and bathed with a solution of pure soricidin for 10 minutes. The nerve tissue was next immersed in a cuvette containing very low calcium ion concentration and a baseline fluorescence value recorded. A bolus of calcium chloride (to a final concentration of 5 mM) was added and, after 5 minutes, the fluorescence was determined. Finally, a bolus of potassium chloride was added to the preparation to a final concentration of 20 mM. The fluorescence was again determined. The control situation was exclusion of the soricidin, substituting instead a sham solution of buffered saline. As shown in FIG. 17, in soricidin treated nerves, the increase in fluorescence because of the formation of the FURA/Calcium complex was 92% less than in control situation. This showed that soricidin effectively blocks the general and voltage-gated calcium channels of neural tissue.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Christenbury P A (1966) MA Thesis. A study of the ecology of *Blarina brevicauda* in North Carolina and of the effect of shrew toxin on the liver and kidneys of mice. Wake Forest College, Winston-Salem, N.C., U.S.A.

Daisuke K & Kaoru Y (1997) Sagami Chemical Research Center, Japan Patent Office Publication Number 10-236963 (Date of publication of application: 08.09.1998)

Dufton M (1982) Pharmac. Ther. 53: 199-215

Ellis S & Krayer O (1955) J Pharm Exper Therapeutics 114: 127-137

Eng J (1993) USPTO Application No. 066480

George S et al. (1986) Am. Soc. Mammal. 261: 1-9

Martin I (1981) J. Mamm. 62: 189-192

Pohl M & Wank S A (1998) J Biol Chem 273: 9778-9784

Zhuang, L., Peng, J. B., Tou, L., Takanaga, H., Adam, R. M., Hediger, M. A. & Freeman, M. R. (2002) Laboratory Investigations 82:1755-1764

Peng, J. B., Zhuang, L., Berger, U. V., Adam, R. M., Williams, B. J., Brown, E. M., Hediger, M. A. & Freeman, M. R. (2001) Biochem. Biophys. Res. Comm. 282: 729-734 see above, this is a duplicateCai, Z., Xu, C., Xu, Y., Lu, W., Chi, C., Shi, Y. & Wu. J. (2004) Biochemistry, 43: 3764-3771

(den Dekker, E., Hoenderop, J. G. J., Nilius, B. & Bindels, R. J. M. (2003) Cell Calcium, 33: 497-507

Lecchi, P., Loh, Y. P., Snell, C. R. & Pannell, L. K. Biochem. Biophys. Res. Comm. 232: 800-805

Montel, C. (2003) Cell Calcium, 33: 409-417

---

We claim:

1. A recombinant expression vector comprising a nucleic acid sequence encoding a peptide comprising all or part of the amino acid sequence (SEQ ID NO: 1), wherein the amino acid sequence has paralytic activity.

2. The vector of claim 1, wherein the peptide comprises a portion consisting of between 10 and 54 consecutive amino acids of the amino acid sequence of SEQ ID NO: 1.

3. The vector of claim 1, wherein the peptide comprises a fragment of between 10-15, 15-20, 20-24, 25-35, 35-45 or 45-54 amino acids of SEQ ID NO: 1.

4. The vector of claim 1, wherein the peptide comprises a portion consisting of between 40 and 54 amino acids of SEQ ID NO: 1.

5. The vector of claim 1, wherein the peptide consists of between 40 and 54 amino acids of SEQ ID NO: 1.

6. The vector of claim 1, wherein the peptide comprises a portion consisting of a fragment of 45-50, 45-52, 35-45 or 25-35 amino acids of SEQ ID NO: 1.

7. The vector of claim 1, wherein the amino acid sequence has at least 80% sequence identity to SEQ ID NO: 1.

8. The vector of claim 1, wherein the amino acid sequence has at least 90% sequence identity to SEQ ID NO: 1.

9. The vector of claim 1, wherein the nucleic acid sequence encodes for the peptide consisting of SEQ ID NO: 1.

10. The vector of claim 1, wherein the nucleic acid sequence is a cDNA sequence.

11. The vector of claim 1, wherein the vector comprises a selectable marker.

12. The vector of claim 1, wherein the vector comprises regulatory sequences for the transcription and translation of the peptide.

13. The vector of claim 1, wherein the vector is a viral vector.

14. The vector of claim 13, wherein the viral vector is a baculovirus vector.

15. The vector of claim 13, wherein the viral vector is a vaccinia viral vector

16. The vector of claim 13, wherein the viral vector is targeted against an invertebrate pest.

17. The vector of claim 16, wherein expression of the nucleic acid sequence immobilizes the invertebrate pest through the paralytic activity of the amino acid sequence.

18. An isolated transformed host cell comprising the vector of claim 1.

19. The isolated transformed host cell of claim 18, wherein the host cell is a eukaryotic cell.

20. The isolated transformed host cell of claim 18, wherein the host cell is a prokaryotic cell.

* * * * *

SEQUENCE LISTING

```
<160> NUMBER OF SEQ ID NOS: 2

<210> SEQ ID NO 1
<211> LENGTH: 54
<212> TYPE: PRT
<213> ORGANISM: Blarina brevicauda

<400> SEQUENCE: 1

Asp Cys Ser Gln Asp Cys Ala Ala Cys Ser Ile Leu Ala Arg Pro Ala
1               5                   10                  15

Glu Leu Asn Thr Glu Thr Cys Ile Leu Glu Cys Glu Gly Lys Leu Ser
            20                  25                  30

Ser Asn Asp Thr Glu Gly Gly Leu Cys Lys Glu Phe Leu His Pro Ser
        35                  40                  45

Lys Val Asp Leu Pro Arg
    50

<210> SEQ ID NO 2
<211> LENGTH: 54
<212> TYPE: PRT
<213> ORGANISM: Blarina brevicauda

<400> SEQUENCE: 2

Asp Cys Ser Gln Asp Cys Ala Ala Cys Ser Ile Leu Ala Arg Pro Ala
1               5                   10                  15

Glu Leu Asn Thr Glu Thr Cys Ile Leu Glu Cys Ala Gly Lys Leu Ser
            20                  25                  30

Ser Asn Asp Thr Glu Gly Gly Leu Cys Lys Glu Phe Leu His Pro Ser
        35                  40                  45

Lys Val Asp Leu Pro Arg
    50
```